(12) United States Patent
Notté et al.

(10) Patent No.: US 8,829,222 B2
(45) Date of Patent: Sep. 9, 2014

(54) PROCESS FOR THE MANUFACTURE OF DIALKYLPHOSPHITES

(75) Inventors: Patrick Notté, Wavre (BE); Albert Devaux, Mont-Saint-Guibert (BE)

(73) Assignee: Straitmark Holding AG, Zug (CH)

( * ) Notice: Subject to any disclaimer, the term of this patent is extended or adjusted under 35 U.S.C. 154(b) by 0 days.

(21) Appl. No.: 13/322,438

(22) PCT Filed: May 28, 2010

(86) PCT No.: PCT/EP2010/057423
§ 371 (c)(1),
(2), (4) Date: Feb. 10, 2012

(87) PCT Pub. No.: WO2010/136564
PCT Pub. Date: Dec. 2, 2010

(65) Prior Publication Data
US 2012/0130109 A1    May 24, 2012

(30) Foreign Application Priority Data
May 28, 2009  (EP) .................................... 09161393

(51) Int. Cl.
*C07F 9/38*  (2006.01)
*C07F 9/142* (2006.01)
*C07F 9/141* (2006.01)

(52) U.S. Cl.
CPC .................................. *C07F 9/1411* (2013.01)
USPC .......................................... 558/114; 562/24

(58) Field of Classification Search
USPC ........................................... 558/114; 562/24
See application file for complete search history.

(56) References Cited

U.S. PATENT DOCUMENTS

| 4,342,709 A | 8/1982 | Jaffe |
| 5,344,951 A | 9/1994 | Kadkhodayan |

FOREIGN PATENT DOCUMENTS

| CN | 101250199 | 8/2008 |
| DE | 128755 | 12/1977 |
| DE | 222596 | 5/1985 |
| DE | 4121696 | 1/1993 |
| HU | 196817 | 1/1989 |
| HU | 199149 | 1/1990 |
| HU | 207334 | 3/1993 |
| WO | 2007024742 | 3/2007 |
| WO | 2009068636 | 6/2009 |
| WO | 2010055056 | 5/2010 |

OTHER PUBLICATIONS

Cason and Baxter, "Reaction of Trialkyl Phosphites with Methanol," Sep. 1, 1958.

*Primary Examiner* — Kristin Vajda
(74) *Attorney, Agent, or Firm* — Samuel Digirolamo; Husch Blackwell LLP

(57) ABSTRACT

A process for the manufacture of dialkyl phosphites is disclosed. In detail, dialkyl phosphites are prepared starting from $P_4O_6$, or partially hydrated species thereof cumulatively P—O, by reacting specific molar ratios of alcohol and P—O, containing from 1 to 6 P—O—P bonds in the molecule, in the presence of trialkylphospite (TAP) to thus yield high purity and high yield of dialkyl phosphites. The P—O reactant is preferably represented by liquid $P_4O_6$.

14 Claims, No Drawings

PROCESS FOR THE MANUFACTURE OF DIALKYLPHOSPHITES

CROSS REFERENCE TO RELATED APPLICATIONS

This Application is a U.S. National Phase patent application of International Application PCT/EP2010/057423, filed 28 May 2010, which claims the benefit of priority from European Patent Application No. 09161393.5 filed on 28 May 2009. The disclosures of International Application PCT Application No. PCT/EP2010/057423 and European Patent Application No. 09161393.5 are incorporated herein by reference.

The invention concerns a beneficial method for the manufacture of dialkyl phosphites starting from P—O components containing from 1 to 6 P—O—P bonds in the molecule comprising the steps of reacting a mixture of an alcohol and the P—O, in specifically defined molar ratios, with a tri-alkyl phosphite (TAP) whereby the level of tri-alkyl phosphite required for the conversion is related to the number of P—O—P bonds in the P—O component. The P—O is added, simultaneously with or separately from the TAP, to a reaction medium comprising the alcohol and reacted followed by recovering the dialkyl phosphite formed in a manner known per sé. In a preferred execution, the P—O is represented by liquid $P_4O_6$ and compounds having from 2 to 6 P—O—P bonds.

Dialkyl phosphites have been known for a long time and their importance as intermediates, among others, for synthesizing desirable compounds had been established accordingly. A large variety of approaches had been investigated for the manufacture of dialkylphosphites. CN 101250199 pertains to a method for preparing diisopropyl phosphite from $PCl_3$ and isopropanol. DE 4121696 describes a process for the preparation of dialkyl phosphites. The treatment of a mixture of methyl- and dimethyl phosphite with acetic anhydride and methanol in benzene resulted in a product containing a high level of dimethyl phosphite. Several publications, HU 207334, HU 199149 and HU 196817, disclose a process for the manufacture of dialkyl phosphites starting from $PCl_3$.

DD 108755 describes the reaction of $P_4O_6$ vapor and methanol vapour to thus yield a mixture of liquid monoester and gaseous diester.

U.S. Pat. No. 4,342,709 describes a process of producing diethyl phosphites by reacting an excess of triethyl phosphite with phosphorous acid. The triethyl reactant is usually added in excess of 7-10% beyond stoichiometric needs. The process starts from a strictly anhydrous phosphorous acid. To avoid negatives attached to the absorption of water, the phosphorous acid is added under inert gas purging. DD 128755 describes a continuous process for preparing dialkyl phosphites starting from phosphorus trichloride and aliphatic alcohols in the presence of an inert solvent. DOS 1 668 031 pertains to the manufacture, in high yields and purity, of dialkyl phosphites starting from primary or secondary linear or branched alcohols, having at least 5 carbon atoms, with phosphorous acid in an excess of at least 45%.

DD 116457 pertains to a continuous process for the manufacture of mono- and di-alkyl phosphites by reacting: a mixture of alcohol and alkyl phosphite or a mixture of mono- and di-alkyl phosphites to which mixture is added technical grade P(III)-oxide containing elementary phosphorus, while purging with technical nitrogen followed by a distillative separation of the mono- and di-alkyl phosphites formed. DD 108755 divulges a process for the continuous preparation of mixtures of mono- and di-alkyl phosphites by reacting $P_4O_6$ with alcohols in the gaseous phase with high yields. DD 222596 concerns a method for preparing pure alkyl- or aryl-diesters of phosphorous acid starting from a mixture of mono- and di-ester phosphites. This mixture is dissolved in an inert organic solvent and the mono-species is precipitated by leading ammonia gas through the mixture.

U.S. Pat. No. 5,344,951 describes a process for preparing di-esters of phosphorous acid whereby a phosphorous acid solution and a solvent are reacted with an excess of monohydric alcohol to thus yield dihydrocarbyl phosphite. WO 2004/024742 concerns a method for the joint manufacture of diethyl phosphite and ethylchloride whereby one reacts ethanol and phosphorous trichloride in the presence of an additive from the group of tri-ethyl phosphite, diethyl phosphite and/or ethylchloride.

The prior art unequivocally shows that the dialkyl phosphite manufacturing technology while deserving substantial technological and economical improvements has been substantially stagnant for a long time, at least had not offered any viable solution for a meaningful improvement. The art technology is frequently cumbersome, time consuming, uneconomical and not adapted to the actual and foreseeable commercial needs.

It is a major object of this invention to provide a significantly improved process for the manufacture of dialkyl phosphites. Yet another object of this invention aims at providing an improved chlorine free process for the manufacture of dialkyl phosphites. It is another object of this invention to provide a method for the manufacture of dialkyl phosphites from reactants broadly other than mixtures of mono and dialkyl phosphites e.g. pure monoalkyl phosphites. Still another aim of this invention is to provide a one-step manufacture of dialkyl phosphites starting from liquid $P_4O_6$. Still another object herein envisages a method for the manufacture of dialkyl phosphites of improved purity and selectivity commensurate with prevailing needs. Yet another objective herein aims at providing dialkyl phosphites at economically favorable conditions. Still another object of this invention aims at providing technology which can serve for the beneficial manufacture of phosphonobutane tricarboxylic acid (PBTC).

The term "percent" or "%" as used throughout this application stands, unless defined differently, for "percent by weight" or "% by weight". The term "ppm" stands for "parts per million". The terms "$P_2O_3$" and "$P_4O_6$" can be used interchangeably. The term "liquid $P_4O_6$" embraces neat $P_4O_6$ in the liquid state, solid $P_4O_6$ and gaseous $P_4O_6$, preferably liquid $P_4O_6$. The term "ambient" with respect to temperature and pressure generally means usually prevailing terrestrial conditions at sea level e.g. temperature is about 18° C. to 25° C. and pressure stands for 990-1050 mm Hg.

The foregoing and other objectives can now be met by a new manufacturing arrangement for converting phosphorus oxides to substantially pure dialkyl phosphites. In more detail, this invention pertains to a process for the manufacture of dialkyl phosphites starting from P—O components containing from 1 to 6 P—O—P bonds in the molecule comprising the step of:

a) reacting a mixture, of R'OH and the P—O component, expressed in molar ratios of R'OH:P—O of at least 1:1 to 6:1,
wherein R' is selected from alkyl groups having from 1 to 20 carbon atoms in branched or linear configuration; and
trialkyl phosphite, TAP, $(P(OA)_3)$;
wherein A stands for linear or branched alkyl groups having from 1 to 20 carbon atoms;
whereby the minimum number of mole(s) of TAP, per P atom in the P—O molecule, required for the process (and for the stoichiometric conversion of one mole of said P—O to dialkyl phosphite), "z", is determined by z=2n−m, where n is the number of P atoms in the P—O molecule and m is the number of P—O—P bonds in the P—O molecule;

by adding the P—O, simultaneously with or separately from the TAP, to a reaction medium comprising the R'OH; and bringing the reaction mixture to a temperature in the range of from 40° C. to 180° C., preferably from 70° C. to 150° C., particularly from 90° C. to 130° C., for a period of 10 minutes to 10 hours, preferably from 15 minutes to 6 hours.

In a preferred execution of this invention, the dialkylphosphite is prepared by adding $P_4O_6$, to the reaction medium simultaneously with or separately from the TAP. The reaction medium is generally the alcohol R'OH itself although a suitable solvent which is inert in relation to P—O, R'OH and TAP, can be used optionally. Preferred suitable solvents are as follows: anisole; fluorobenzene; chlorinated hydrocarbons such as chlorobenzene, tetrachloroethane, tetrachloroethylene; polar solvents like sulfolane, diglyme, glyme, diphenyl oxide, polyalkylene glycol derivatives with capped OH groups such as OR where R is a low alkyl group; aliphatic hydrocarbons such as hexane, heptane, cyclohexane; non-cyclic ethers like dibutyl ether, diisopropyl ether, and dipentyl ether; cyclic ethers like tetrahydrofuran and dioxane; aromatic hydrocarbons like toluene, xylene; organic nitriles like acetonitrile; silicon fluids like polymethylphenyl siloxane or mixtures thereof.

The $P_4O_6$ can be represented by a substantially pure compound containing at least 85%, preferably more than 90%; more preferably at least 95% and in one particular execution at least 97% of the $P_4O_6$. While tetraphosphorus hexa oxide, suitable for use within the context of this invention, can be manufactured by any known technology, in preferred executions the hexa oxide can be prepared in accordance with the method of WO 2009/068636 and/or PCT/EP2009/064988, entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. The hexa oxide so prepared is a pure product containing usually at least 97% of the oxide. The $P_4O_6$ so produced is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds. The reaction product can, in one preferred execution, be quenched to a temperature below 350 K.

The term "liquid $P_4O_6$" embraces, as spelled out, any state of the $P_4O_6$. However, it is presumed that the $P_4O_6$ participating in a reaction at a temperature of from 40° C. to 180° C. is necessarily liquid or gaseous although solid species can, academically speaking, be used in the preparation of the reaction medium.

The P—O component can be represented by $P_4O_6$, or partially hydrated species thereof, containing from 1 to 6 P—O—P bonds in the molecule. Examples of suitable species of the P—O component include: pyrophosphorous acid, $H_4P_2O_5$, containing one P—O—P bond; $P_4O_6$ containing six P—O—P bonds; and partially hydrated species thereof containing 2, 3, 4 and 5 P—O—P bonds respectively. Partially hydrated $P_4O_6$ can lead to hydrolysis products containing 2, 3, 4 or 5 P—O—P bonds. For reasons of convenience and operational expertise, the P—O component is preferably represented by $P_4O_6$ of high purity containing very low levels of impurities, in particular elemental phosphorus, $P_4$, at a level below 1000 ppm, usually below 500 ppm and preferably no more than 200 ppm, expressed in relation to the $P_4O_6$ being 100%. The P—O component can be represented by uniform ingredients having e.g. a uniform number of P—O—P bonds or by mixtures having a distribution of P—O—P bonds as may occur in partially hydrated species of $P_4O_6$. Obviously, in such case the number of P—O—P stands for an average number of P—O—P bonds. Suitable P—O can also be prepared starting from $PCl_3$ by partial hydrolysis, or by reacting $PCl_3$ and phosphorous acid or by reacting $P_4O_6$ and phosphorous acid or by partial hydrolysis of $P_4O_6$. The P—O can be represented by mixtures/combinations of different reagents e.g. $PCl_3$, phosphorous acid and water subject to the presence of at least one P—O—P bond in the molecule. The level of water to be employed is limited (in molar terms) to 4 $H_2O$ or less per $P_4O_6$. In the event a chlorine containing starting materials, e.g. $PCl_3$ and combinations thereof, are used the level of chlorine shall be kept below 1000 ppm, usually below 500 ppm, preferably below 200 ppm, expressed in relation to the P—O material being 100%.

Trialkyl phosphites, TAP, $(P(OA)_3)$, are well known materials a fair number of which are commercially available or can be made available routinely in accordance with needs. Examples of a variety of commercially available species are as follows: tri-methyl phosphite; tri-ethyl phosphite; tri-n-propyl phosphite; tri-isopropyl phosphite; tri-n-butyl phosphite; tri-isobutyl phosphite; tri-n-pentyl phosphite; tri-t-butyl phosphite; tri-2-ethylhexyl phosphite; tri-octadecyl phosphite; tri-n-decyl phosphite; tri-n-octyl phosphite; tri-n-dodecyl phosphite; tri-n-hexyl phosphite; tri-(propyl-2,2-dimethyl) phosphite; and tri-(8-methyl nonyl) phosphite.

The alkyl group, A, in the TAP for use in this invention is selected from linear or branched alkyl groups having from 1 to 20 carbon atoms, preferably from 1 to 12 carbon atoms, in one particular execution from 1 to 8 carbon atoms. The alkyl groups may be the same or different, preferably they are the same. The minimum number of moles of TAP, per P atom in the P—O, required for converting one mole of P—O to dialkyl phosphites, and, thus, for the inventive process, "z" is determined with the aid of the equation:

$$z=2-m$$

whereby m is the number of P—O—P bonds in the P—O molecule and n is the number of P atoms in that molecule.

The R'OH is represented by alcohols having an alkyl group R' of from $C_1$ to $C_{20}$, in linear or branched structure, preferably an alkyl group having from 1 to 12 carbon atoms. The R'OH is preferably used in relation to P—O in molar ratios of from R'OH:P—O of at least 1:1 to 6:1. The ratios R'OH:P—O of 1:1 to 6:1 are related to the number of P—O—P bonds in the P—O compound. The term "at least" means that the level of R'OH can be increased to e.g. 8:1 without adversely affecting the system. Any excess of R'OH can routinely be recycled into the system and thus doesn't affect the economics of the inventive method. While the alkyl groups of the alcohol, R'OH, and the TAP can be varied independently over the inventive ranges, it is preferred to use identical alkyl groups in both the R'OH and the TAP, i.e., R'=A.

The reaction in accordance with this invention is conducted in a manner routinely known in the domain of the technology. As illustrated in the experimental showings, the method can be conducted by combining the essential reaction partners and heating the reaction mixture to a temperature usually within the range of from 45° C. to 180° C., more preferably 70° to 150° C., in particular 90 to 130° C. The upper temperature aims at preventing any substantial undue decomposition of the reactants or of the intermediates formed in these reactions. It is understood and well known that the decomposition temperature of the reaction partners and intermediates can vary depending upon physical parameters, such as pressure and the qualitative and quantitative parameters of the ingredients in the reaction mixture.

The inventive reaction can be conducted at ambient pressure and, depending upon reaction temperature, under distillation thereby also eliminating possibly under vacuum potential alcohol excess. The duration of the reaction can vary from virtually instantaneous, e.g. 10 minutes, to an extended period of e.g. 10 hours. In one method set up, the P—O, the alcohol and the TAP are added to the reactor followed by heating this mixture gradually to a temperature of from 70° to 150° C. This reaction can be carried out under ambient, possibly reduced, pressure with or without distillation.

In another operational arrangement, the reaction can be conducted in a closed vessel under autogeneous pressure built up. In this method, the reaction partners, in total or in part, are added to the reaction vessel at the start. In the event of partial mixture, the additional reaction partner can be gradually added, as soon as the effective reaction temperature has been reached.

In yet another operational sequence, the reaction can be conducted in a combined distillation and pressure arrangement. Specifically, the reaction vessel containing the reactant mixture is kept under ambient or reduced pressure at the selected reaction temperature. The mixture is then, possibly continuously circulated through a reactor operated under autogeneous (autoclave principle) pressure build up thereby gradually adding the additional reaction partners in accordance with needs. The reaction is substantially completed under pressure and the reaction mixture then leaves the closed vessel and is recycled to the reactor where excess alcohol distillation can occur depending upon the reaction variables, particularly the temperature and the pressure.

The foregoing process variables thus show that the reaction can be conducted by a variety of substantially complementary arrangements. The reaction can thus be conducted as a batch process by heating the initial reactants in a (1) closed vessel under autogeneous pressure built up, or (2) under reflux conditions, or (3) under distillation of non-reacted ingredients, to a temperature preferably in the range of from 70° C. to 150° C. In a particularly preferred embodiment, the reaction is conducted in a closed vessel at a temperature in the range of from 100° C. to 150° C. coinciding particularly with the gradual addition of residual ingredients.

In another approach, the reaction is conducted as a continuous process, possibly under autogeneous pressure, whereby the reactants are continuously injected into a reaction mixture at a temperature preferably in the range of from 70° C. to 150° C.

In yet another arrangement, the method can be represented by a semi-continuous set-up whereby the reaction is conducted continuously whereas preliminary reactions e.g. between the $P_4O_6$ and the alcohol, can be conducted batch-wise.

The dialkyl phosphite reaction products can, if needed, be recovered from the reaction product by conventional means including, in particular, vacuum distillation.

The dialkyl phosphites can be used as intermediates, e.g. for beneficially synthesizing compounds which were known to be difficult to make. As an example, 2-phosphonobutyl-1,2,4-tricarboxylic acid can be made starting from dialkylphosphites as follows:

1: reacting dimethyl phosphite with methylmaleate; followed by

2: reacting the system resulting from 1: with methyl acrylate in the presence of sodium methoxide; followed by 3: hydrolysing the ester groups formed under 2: with water in the presence of hydrochloric acid.

Accordingly, in a further aspect of the invention, there is provided a process for preparing 2-phosphonobutyl-1,2,4-tricarboxylic acid by preparing dimethylphosphite according to the method of the invention and further conversion to 2-phosphonobutyl-1,2,4-tricarboxylic acid as described above.

The invention is illustrated by the following examples without limiting it thereby.

EXAMPLES

Example 1

$P_4O_6$ and methanol were reacted to yield a 1:1 mixture of dimethylphosphite and monomethylphosphite. The mixture, containing 7.54 g of dimethylphosphite and 6.59 g of monomethyl phosphate, and 2.2 g of methanol (0.0685 mole of each material), were mixed with 8.47 g (0.0685 mole) of trimethyl phosphite and heated under stirring under nitrogen at a temperature of 95° C. for 3 hours. $^{31}P$ NMR analysis of the crude reaction mixture showed the presence of 1.2% w/w (1.6 mole %) of $H_3PO_3$; 25.1% w/w (25.1 mole %) of mono methylphosphite and 72.6% w/w (69.7 mole %) of dimethylphosphite.

Example 2

22 g (0.1 mole) of $P_4O_6$ heated at 40° C. were added dropwise over 20 minutes to 55.3 g (1.2 moles) of absolute ethanol under stirring. Then, 33.23 g (0.2 moles) of triethylphosphite were added to the reaction mixture and temperature was gradually increased under stirring and nitrogen up to between 80 and 85° C. while excess ethanol is distilled off. After 3 hours of additional heating at 95° C. $^{31}P$ NMR analysis showed 18.8% w/w (22.4 mole %) of mono-ethylphosphite; 80.2% w/w (76.3 mole %) of diethylphosphite and 0.5% w/w (0.8 mole %) of phosphorous acid.

Example 3

22 g (0.1 mole) of $P_4O_6$ heated at 40° C. were added dropwise over 20 minutes to 55.3 g (1.2 moles) of absolute ethanol under stirring. Then, 36.6 g (0.22 mole) of triethylphosphite were added to the reaction mixture. Heating of the reaction mixture under stirring and nitrogen was applied with gradual increase of the reaction temperature up to 97° C. for 6 hours with distillation of excess ethanol. $^{31}P$ NMR analysis of the crude reaction mixture showed 18.2% w/w (21.7 mole %) of mono-ethylphosphite; 80.8% w/w (77 mole %) of diethylphosphite and 0.5% w/w (0.8 mole %) of phosphorous acid

Example 4

22 g (0.1 mole) of $P_4O_6$ heated at 40° C. were added drop wise over 20 minutes to 62.7 g (1.34 moles) of absolute ethanol under stirring. Unreacted ethanol was distilled off by heating to 95° C. At 84° C., 36.6 g (0.22 mole) of triethylphosphite were added dropwise to the reaction mixture which was further heated to 92-100° C. for 4 hours. $^{31}P$ and $^{1}H$ NMR analysis of the crude reaction mixture showed 6.8% w/w (8.4 mole %) mono-ethylphosphite; 93.2% w/w (91.6 mole %) of diethylphosphite.

Example 5

22 g (0.1 mole) of $P_4O_6$ heated at 40° C. were added drop wise over 40 minutes to 52.9 g (1.65 moles) of dried methanol under stirring. Excess methanol was distilled off and 27.5 g (0.22 moles) of trimethyl phosphite added at 80° C. drop wise. The resulting mixture was then heated at 95° C. for 3 hours and 30 minutes. $^{31}P$ analysis of the crude reaction mixture showed 19.4% w/w (21.7 mole %) mono-methylphosphite and 78.6% w/w (76.6 mole %) of dimethylphosphite.

The invention claimed is:

1. A process for the manufacture of dialkyl phosphites starting from a P—O component having from 1 to 6 P—O—P bonds in the molecule comprising the step of:
   a) reacting a mixture of R'OH and the P—O component expressed in molar ratios of R'OH:P—O of at least 1:1 to 6:1,
   wherein R' is selected from alkyl groups having from 1 to 20 carbon atoms in branched or linear configuration; and $P(OA)_3$ (trialkyl phosphite, TAP),
   wherein A stands for linear or branched alkyl groups having from 1 to 20 carbon atoms;
   whereby the minimum number of mole(s) of TAP, per P atom in the P—O molecule, required for the process, is represented by "z", and z is determined by the formula $z=2n-m$,
   wherein;
   n is the number of P atoms in P—O and
   m is the number of P—O—P bonds in P—O;
   by adding the P—O, simultaneously with or separately from the TAP, to a reaction medium comprising the R'OH; and bringing the reaction mixture to a temperature in the range of from 40° C. to 180° C. for a period from 10 minutes to 10 hours.

2. The process in accordance with claim 1 wherein the P—O has from 2 to 6 P—O—P bonds.

3. The process in accordance with claim 1, wherein the P—O is represented by liquid $P_4O_6$.

4. The process in accordance with claim 1, wherein the P—O is added to the reaction medium comprising the R'OH and the TAP.

5. The process in accordance with claim 1, wherein the P—O has less than 1000 ppm of elemental phosphorus, $P_4$, expressed in relation to P—O being 100%.

6. The process in accordance with claim 1, wherein the alkyl groups in the alcohol, R'OH, and TAP are identical.

7. The process in accordance with claim 1, wherein the molar ratio of R'OH:P—O is in the range of from 1:1 to 8:1.

8. The process in accordance with claim 1, wherein the trialkyl phosphite is selected from the group of: tri-methyl phosphite; tri-ethyl phosphite; tri-n-propyl phosphite; tri-isopropyl phosphite; tri-n-butyl phosphite; tri-isobutyl phosphite; tri-n-pentyl phosphite; tri-t-butyl phosphite; tri-2-ethylhexyl phosphite; tri-n-decyl phosphite; tri-n-octyl phosphite; tri-n-dodecyl phosphite; tri-n-hexyl phosphite; tri-(propyl-2,2-dimethyl) phosphite; and tri-(8-methyl nonyl) phosphite.

9. The process in accordance with claim 1, wherein the P—O is added to the reaction medium comprising water in a molar level of 4 or less $H_2O$ per P—O.

10. The process in accordance with claim 1, wherein the alkyl groups in the alcohol and the TAP have from 1 to 12 carbon atoms.

11. The process in accordance with claim 1, wherein the alkyl group in the alcohol has from 1 to 8 carbon atoms.

12. The process in accordance with claim 1, wherein the reaction is conducted for a period of 15 minutes to 6 hours at a temperature from 70° C. to 150° C.

13. The process in accordance with claim 1, wherein the P—O compound prepared starting from $PCl_3$ having less than 400 ppm of chlorine, expressed in relation to the P—O compound (100%).

14. The process in accordance with claim 1, wherein the alcohol is methanol and the TAP is $P(OCH_3)_3$, further comprising the steps of
   b) reacting the dimethyl phosphate obtained in step a) with methylmaleate; followed by
   c) reacting the system resulting from step b) with methyl acrylate in the presence of sodium methoxide; followed by
   d) hydrolysing the ester groups formed in step c) with water in the presence of hydrochloric acid,
   to obtain 2-phosphonobutyl-1,2,4-tricarboxylic acid.

* * * * *